United States Patent [19]

Takeda et al.

[11] Patent Number: 5,158,891
[45] Date of Patent: Oct. 27, 1992

[54] PLASMID CONTAINING A GENE FOR TETRACYCLINE RESISTANCE AND DNA FRAGMENTS DERIVED THEREFROM

[75] Inventors: Yasuhiko Takeda; Mikio Fujii; Yukihiro Nakajo, all of Nobeoka; Sadao Isshiki, Sashima, all of Japan

[73] Assignee: Asahi Kasei Kogyo Kabushiki Kaisha, Osaka, Japan

[21] Appl. No.: 492,227

[22] Filed: Mar. 13, 1990

Related U.S. Application Data

[63] Continuation of Ser. No. 17,055, Feb. 20, 1987, abandoned, which is a continuation-in-part of Ser. No. 766,282, Aug. 16, 1985, abandoned.

[30] Foreign Application Priority Data

Aug. 21, 1984 [JP] Japan ............................ 59-172395
Aug. 21, 1984 [JP] Japan ............................ 50-172396
Oct. 30, 1984 [JP] Japan ............................ 59-226651

[51] Int. Cl.$^5$ .................... C12N 15/77; C12N 15/65; C12N 15/00
[52] U.S. Cl. ............................ 435/320.1; 435/172.3; 435/252.32; 435/843; 536/27; 935/29
[58] Field of Search ........... 435/320, 172.1, 172.3, 435/843, 252.3, 252.32; 536/27; 935/29, 14

[56] References Cited

U.S. PATENT DOCUMENTS

| | | | |
|---|---|---|---|
| 3,929,571 | 12/1975 | Kubota et al. | 435/115 |
| 4,489,160 | 12/1984 | Katsumata et al. | 435/253 |
| 4,500,640 | 2/1985 | Katsumata et al. | 435/253 |
| 4,514,502 | 4/1985 | Miwa et al. | 435/252.32 |
| 4,710,471 | 12/1987 | Katsumata et al. | 435/252.32 |

FOREIGN PATENT DOCUMENTS

| | | |
|---|---|---|
| 0058889 | 9/1982 | European Pat. Off. . |
| 0077548 | 4/1983 | European Pat. Off. . |
| 0078537 | 5/1983 | European Pat. Off. . |
| 0082485 | 6/1983 | European Pat. Off. . |
| 0088166 | 9/1983 | European Pat. Off. . |
| 58-216199 | 12/1983 | Japan . |
| 59-120090 | 7/1984 | Japan . |
| 59-143591 | 8/1984 | Japan . |
| 2165546 | 4/1986 | United Kingdom . |

OTHER PUBLICATIONS

Bergey's Manual of Determinative Bacteriology, 8th Ed., R. E. Buchanan and N. E. Gibbons, Co–Editors.
The American Type Culture Collection, Catalogue of Strains I, 14th ed.; 1980.
Old et al., Principles of Gene Manipulation, published by the University of California Press, 1980, pp. 9 and 23.
Maniatis et al., Molecular Cloning, a Laboratory Manual, published by Cold Spring Harbor Laboratory, 1982, p. 136.
Foster, T. J., 1983, Microbiological Reviews, pp. 361–409.
Bolivar et al. (1977), Gene, vol. 2, pp. 95–113.
Maniatis et al. (1982), Molecular Cloning, p. 72.
Rockhill et al., *Antimicrobial Agents and Chemotherapy*, vol. 21, pp. 842–843, 1982 (May).
Tikchonenko et al, Gene 4, pp. 195–212 (1978).

*Primary Examiner*—Richard A. Schwartz
*Assistant Examiner*—Richard M. Lebovitz
*Attorney, Agent, or Firm*—Birch, Stewart, Kolasch & Birch

[57] ABSTRACT

A plasmid and a DNA fragment each of which contains a gene for tetracycline resistance derived from a glutamic acid-producing coryneform bacterium, and a coryneform bacterium containing said DNA fragment. The gene for tetracycline resistance derived from a glutamic acid-producing coryneform bacterium is a useful selective marker in effecting the breeding of a glutamic acid-producing coryneform bacterium by genetic recombination. Using the plasmid, the DNA fragment or the coryneform bacterium of the present invention, breeding of the glutamic acid-producing coryneform bacterium can be easily and effectively conducted by means of recombinant DNA technique.

5 Claims, 4 Drawing Sheets

PLASMID CONTAINING A GENE FOR TETRACYCLINE RESISTANCE AND DNA FRAGMENTS DERIVED THEREFROM

This application is a continuation of application Ser. No. 07/017,055 filed on Feb. 20, 1987, now abandoned, which is a continuation-in-part of Ser. No. 06/766,282, filed on Aug. 16, 1985, now abandoned.

BACKGROUND OF THE INVENTION

1. Field of the Invention

This invention relates to a plasmid containing a gene for tetracycline resistance. More particularly, the present invention relates to a plasmid comprising a gene for tetracycline resistance and a gene for replication which are derived from a glutamic acid-producing coryneform bacterium. The present invention also relates to a DNA fragment containing a gene for tetracycline resistance and a microorganism containing the DNA fragment.

In the present specification, restriction endonucleases (hereinafter often referred to simply as "restriction enzyme") represented by the following abbreviations are restriction endonucleases respectively obtained from the following microorganisms.

| Abbreviation | Microorganism |
| --- | --- |
| EcoRI | *Escherichia coli* RY13 |
| HindIII | *Haemophilus influenza* Rd |
| PstI | *Providencia stuartii* 164 |
| BamHI | *Bacillus amyloliquefaciens* H |
| XbaI | *Xanthomonas badrii* |
| BglII | *Bacillus globigii* |
| SalI | *Streptomyces albus* G |
| HaeIII | *Haemophilus aegyptius* |

2. Discussion of Related Art

Conventionally, it is known that a glutamic acid-producing coryneform bacterium produces L-glutamic acid in high yield and that a certain mutant or variant of the glutamic acid-producing coryneform bacterium produces other amino acids such as L-lysine, and purine nucleotides such as an inosinic acid. Such a glutamic acid-producing coryneform bacterium and a mutant or variant thereof have been industrially utilized for producing the amino acids and purine nucleotides as mentioned above.

To obtain the coryneform bacterium in a form capable of producing the desired products efficiently in high yield, breeding of the coryneform bacterium is usually effected. Particularly in recent years, the breeding of the glutamic acid-producing coryneform bacterium by transforming the bacterium with a vector containing a gene coding for a certain peptide desired for the production of the intended amino acid has been attempted using recombinant DNA techniques. To effectively attain the transformation of the glutamic acid-producing coryneform bacterium by means of recombinant DNA techniques, it is necessary to use a vector suitable for the transformation. Therefore, various studies have been made on vectors such as a plasmid and a phage. As the plasmid, there are known those which are obtained from glutamic acid-producing coryneform bacteria, such as a plasmid pCG1 (Japanese Patent Application Laid-open Specification No. 57-134500), a plasmid pCG2 (Japanese Patent Application Laid-open Specification No. 58-35197), a plasmid pCG4 (Japanese Patent Application Laid-open Specification No. 57-183799), plasmids pAM330 and pAM286 (Japanese Patent Application Laid-open Specification No. 58-67699) and a plasmid pHM1519 (Japanese Patent Application Laid-open Specification No. 58-77895). However, most of the above-mentioned plasmids do not have a gene which is useful as a selective marker. In effecting genetic recombination, in order to select a bacterium transformed with a recombinant vector, it is necessary that the recombinant vector has a gene useful as a selective marker, such as a gene for drug resistance. For this reason, the above-mentioned plasmids are lacking in practical utility. In order to overcome the disadvantage as mentioned above, various plasmids having a gene for a drug resistance as a selective marker have heretofore been proposed. For example, as the plasmid having a gene for a drug resistance and derived from a glutamic acid-producing coryneform bacterium, the following plasmids have been proposed.

(1) Plasmid pCG11: The plasmid has as a selective marker a gene for streptomycin and spectinomycin resistances which gene is derived from a plasmid pCG4 of a bacterium belonging to Corynebacterium (Japanese Patent Application Laid-open Specification Nos. 57-183799 and 58-105999).

(2) Plasmids pCB101 and pEthr1: The plasmids have as a selective marker a gene for streptomycin and spectinomycin resistances which gene is derived from the above-mentioned plasmid pCG4 (Japanese Patent Application Laid-open Specification No. 58-105999). As mentioned above, all the plasmids pCG11, pCB101 and pEthr1 commonly have a gene derived from a glutamic acid-producing coryneform bacterium as the selective marker, namely a gene for streptomycin and spectinomycin resistances. In other words, with respect to a selective marker derived from a glutamic acid-producing coryneform bacterium, only the gene for streptomycin and spectinomycin resistances is known.

In general, as mentioned above, in order to surely select a bacterium which has been transformed with a recombinant plasmid, a selective marker is needed. On the other hand, to easily ascertain that the recombinant plasmid which is contained in the transformed bacterium has a gene coding for a certain peptide desired for the production of the intended amino acid (desired peptide), it is necessary that the plasmid contains another selective marker. If a plasmid containing such two kinds of selective markers, namely a gene for a first drug resistance and a gene for a second drug resistance, is used, an intended transformant can be easily selected and separated. Illustratively stated, such a plasmid having the two kinds of selective markers is treated with a specific restriction enzyme so that the plasmid is cleaved at an intermediate position of the gene for a first drug resistance. The cleaved plasmid thus obtained is mixed with a gene for the desired peptide and subjected to incubation. During the incubation, some of the cleaved plasmids are caused to have the gene for the desired peptide inserted between both ends of the cleavage of the plasmid, and some of the cleaved plasmids are caused to be religated at both ends of the cleavage of the plasmid. In the former instance, the gene for a first drug resistance is inactivated (inactivation by insertion), so that when the recombinant plasmid having the gene for the desired peptide is used to transform a bacterium, the obtained transformed bacterium which contains the recombinant plasmid having the gene coding for the desired peptide is no longer resistant to the first drug, that is, sensitive to the first drug but resistant to the second drug. At the latter instance, the resultant plasmid has the uncleaved gene for the first drug resistance and, therefore, when such a plasmid is used to transform a bacterium, the obtained transformed bacterium is resistant to both the first and second drugs. In this connection, it is noted that after the transforming operation, the resultant includes, in addition to the transformed bacterium sensitive to the first drug but resistant to the second drug and the transformed bacterium resistant to both the first and second drugs, a bacterium which has failed to be transformed with any of the abovementioned two kinds of plasmids and hence sensitive to both the first and second drugs.

Accordingly, from the above-mentioned three kinds of bacteria in the transformation system, the bacterium transformed with the recombinant plasmid having the gene for the desired peptide can be easily selected and separated by the criterions of the resistance to the first drug and the resistance to the second drug. In this connection, it should be noted that to attain the easy selection and separation of the bacterium transformed with the recombinant plasmid having the gene for the desired peptide, as described above, it is necessary to employ two kinds of selective markers. However, as the selective marker derived from a glutamic acid-producing coryneform bacterium, there is known only one gene, namely, gene for streptomycin and spectinomycin resistances. With such only one selective marker, the easy selection of the transformed bacterium which contains a plasmid having the gene coding for the desired peptide cannot be attained.

Under such a situation, it has been proposed to use, as a second selective marker having a resistance to a drug other than streptomycin and spectinomycin, a gene derived from other bacterium than a glutamic acid-producing coryneform bacterium. As a plasmid containing such a different gene, the following plasmids may be mentioned.

(1) Plasmid pCE54: The plasmid has as a selective marker a gene for tetracycline resistance, a gene for chloramphenicol resistance and a gene for kanamycin resistance which genes are all derived from *Escherichia coli* (Japanese Patent Application Laid-open Specification Nos. 58-105999 and 58-126789).

(2) Plasmid pCB101: The plasmid has as a selective marker a gene for kanamycin resistance which is contained in a plasmid pUB110 derived from a bacterium belonging to Staphylococcus (Japanese Patent Application Laid-open Specification No. 58-105999).

(3) Plasmid pEthr1: The plasmid has as a selective marker a gene for expression of threonine operon which gene is derived from *Escherichia coli*. The use of the plasmid is limited to the transformation of a thr⁻ strain of the coryneform bacteria (Japanese Patent Application Laid-open Specification No. 58-105999).

(4) Plasmid pAJ43: The plasmid has as a selective marker a gene for chloramphenicol resistance which gene is derived from a plasmid pBR325 of *Escherichia coli* (Japanese Patent Application Laid-open Specification No. 59-120090).

(5) Plasmid pAJ655: The plasmid has as a selective marker a gene for chloramphenicol resistance which gene is derived from a plasmid pBR325 of *Escherichia coli* (Japanese Patent Application Laid-open Specification Nos. 58-216199 and 59-120090).

(6) Plasmids pAJ440 and pAJ3148: The plasmid has as a selective marker a gene for kanamycin resistance which gene is derived from a plasmid pUB110 of a bacterium belonging to Staphylococcus (Japanese Patent Application Laid-open Specification No. 58-216199).

However, the second markers contained in the above-mentioned plasmids have the following disadvantage. The above-mentioned second sensitive markers are derived from bacteria other than a glutamic acid-producing coryneform bacterium, that is, the markers are heterogeneous to the coryneform bacterium and, therefore, when such a heterogenous marker is used as the second marker for a host-vector system using as the host a glutamic acid-producing coryneform bacterium, the heterogeneous marker does not sufficiently function and the resistance to the drug is not increased to a sufficient degree. For example, when the gene for tetracycline resistance of the above-mentioned plasmid pCE54, which is derived from *E. coli*, is used as a selective marker for a host-vector system using, as the host, *E.coli* to which the gene for tetracycline resistance of the plasmid pCE54 is homogenous, the minimum tetracycline concentration of a medium at which the growth of the *E.coli* is inhibited (a growth-inhibiting minimum tetracycline concentration) is increased to a value as high as 10 µg/ml. However, when the above-mentioned gene for tetracycline resistance which gene is derived from *E.coli* is used as a selective marker for a host-vector system using as a host a glutamic acid-producing coryneform bacterium to which the above-mentioned gene for tetracycline resistance is heterogenous, the minimum tetracycline concentration at which the growth of the glutamic acid-producing coryneform bacterium is inhibited is only increased from 0.1 µg/ml to 3.2 µg/ml. As a tetracycline concentration as low as 3.2 µg/ml, the selection of the transformed bacterium cannot be sufficiently attained and there is a danger that the selected transformed bacteria is contaminated with an untransformed bacterium. For the abovementioned reasons, the breeding of a glutamic acid-producing coryneform bacterium is conventionally not effectively effected.

SUMMARY OF THE INVENTION

In order to overcome the above-mentioned problem the present inventors have made extensive and intensive studies. As a result, the present inventors have found a plasmid containing a gene for tetracycline resistance derived from a glutamic acid-producing coryneform bacterium and succeeded in isolating the plasmid and the gene, and that the isolated gene is useful as a selective marker for a host-vector system using as the host a glutamic acid-producing coryneform bacterium. The present invention has been made based on such novel findings.

Therefore, it is an object of the present invention to provide a plasmid containing a gene for a specific drug resistance other than a gene for streptomycin and spectinomycin resistance, which is useful for the breeding of a glutamic acid-producing coryneform bacterium by genetic recombination.

It is another object of the present invention to provide a DNA fragment containing the above-mentioned gene for a specific drug resistance.

It is a further object of the present invention to provide a coryneform bacterium containing the above-mentioned DNA fragment.

The foregoing and other objects, features and advantages of the present invention will be apparent from the following detailed description taken in connection with the accompanying drawings in which:

BRIEF DESCRIPTION OF THE DRAWINGS

In the FIGS. 1 to 7, the map positions of the various restriction sites are given as kilobase (hereinafter referred to as "kb") coordinates relative to the XbaI restriction site at 0.0/20.4 kb in FIG. 1, the HindIII restriction site at 0.0/4.8 kb in FIG. 2, the XbaI restriction site at 0.0/10.7 kb in FIG. 3, the XbaI restriction site at 0.0/10.7 kb in FIG. 4, the BamHI restriction site at 0.0/8.4 kb in FIG. 5, the BamHI restriction site at 0.0/7.3 kb in FIG. 6 and the BamHI restriction site at 0.0/8.0 kb in FIG. 7. In FIG. 7, (A) is a DNA fragment obtained by BamHI cleavage of the plasmid pAG3, and (B) is a DNA fragment obtained by BamHI cleavage and BglII cleavage of the plasmid pAG14.

DETAILED DESCRIPTION OF THE INVENTION

Figure 1:
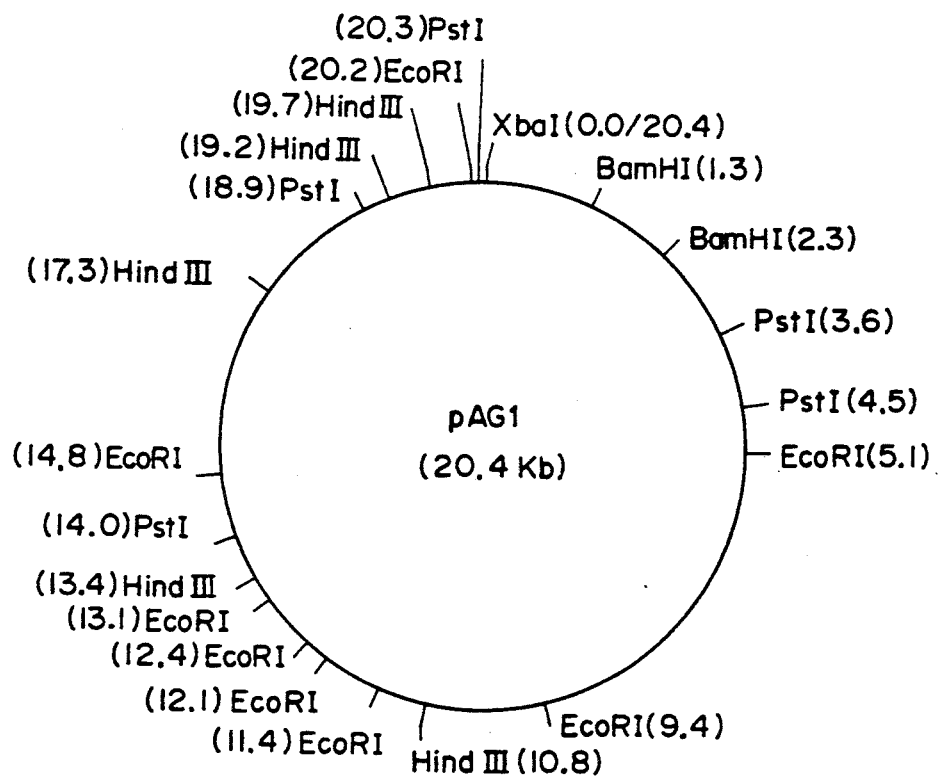
FIG. 1 illustrates the restriction endonuclease cleavage map of a plasmid pAG1 of the present invention.

Essentially, according to the present invention there is provided a plasmid containing a gene for tetracycline resistance derived from a glutamic acid-producing coryneform bacterium.

The gene for tetracycline resistance means a gene coding for such a genetic information that when the gene is expressed in the cell of a microorganism, the resistance to tetracycline which is an antibiotic is conferred on the microorganism.

The glutamic acid-producing coryneform bacterium is a Gram-positive, non-motile and aerobic bacterium which does not form a spore and requires biotin for its growth, and which produces L-glutamic acid in high yield in a medium containing biotin in limited amount, or in a surfactant-added medium containing biotin in high amount. As such a glutamic acid-producing coryneform bacterium, there may be mentioned bacteria belonging to the genus Corynebacterium, Brevibacterium or Microbacterium.

As the plasmid of the present invention, there may be mentioned, for example, a plasmid pAG1. The plasmid pAG1 is obtainable from the microorganism *Corynebacterium melassecola* 22243 which is deposited with the Fermentation Research Institute (hereinafter often referred to as "FRI") under the accession number FERM BP-560. The plasmid pAG1 has a molecular length of about 20.4 kb and the sensitivities of the plasmid pAG1 to various restriction enzymes are as follows.

| Restriction Enzyme | Number of cleavage sites |
|---|---|
| EcoRI | 8 |

-continued

| Restriction Enzyme | Number of cleavage sites |
|---|---|
| HindIII | 5 |
| PstI | 5 |
| BamHI | 2 |
| XbaI | 1 |

The restriction endonuclease cleavage sites (hereinafter often referred to simply as "restriction sites") of the plasmid pAG1 are determined as follows. From the plasmid pAG1, 0.5 μg samples are prepared, and they are digested with the following restriction enzymes in a 20 μl of a suitable buffer at 37° C. for 2 hours. As the restriction enzymes, there are used EcoRI, HindIII, PstI, BamHI and XbaI. Each of the restriction enzymes is used in an amount of 10 units. The digestions are conducted using the restriction enzymes alone and in combination. The thus obtained digests are subjected to 1% (w/v) agarose gel electrophoresis and 4% (w/v) polyacrylamide gel electrophoresis according to the method of Maniatis et al. [T. Maniatis, E. F. Fritsch, J. Sambrook; Molecular Cloning A Laboratory Manual, Cold Spring Harbor Laboratory, Cold Spring Harbor N.Y. p.150-185, 1982]. After completion of the electrophoresis, the gel is dipped in an ethidium bromide solution containing 1 μg/ml of ethidium bromide for 30 minutes to stain the gel. Then, the gel is irradiated with UV light to determine the number of bands which correspond to the number of DNA fragments obtained. The respective molecular lengths of the DNA fragments are determined by comparison of the respective distances of migration of the fragments in electrophoresis with those of the DNA fragments respectively having known molecular lengths. The molecular length of the plasmid pAG1 is calculated by adding the molecular lengths of the respective DNA fragments. Further, based on the results obtained in the above analysis, the distances between two adjacent restriction sites in the plasmid pAG1 and the position of the restriction endonuclease cleavage sites of the plasmid pAG1 are determined. As mentioned above, the respective molecular lengths of the DNA fragments are determined by comparison of the respective distances of migration of the fragments in electrophoresis with those of the DNA fragments respectively having known molecular lengths. In determination of molecular lengths of 0.5 kb or more, there is employed 1% (w/v) agarose gel electrophoresis, whereas in determination of those of about 0.1 kb to less than 0.5 kb, there is employed 4% (w/v) polyacrylamide gel electrophoresis. As such a DNA fragment having a molecular length, DNA fragments obtained by HindIII digestion of λ phage DNA (manufactured and sold by Nippon Gene Co., Ltd., Japan) are used in the case of the agarose gel electrophoresis, the molecular lengths of the fragments being 23130 bp, 9419 bp, 6557 bp, 4371 bp, 2322 bp, 2028 bp, 564 bp and 125 bp in the order of large molecular length. On the other hand, in the case of the polyacrylamide gel electrophoresis, as a DNA fragment having a known molecular length, there are used DNA fragments obtained by HaeIII digestion of φ174 phage DNA (manufactured and sold by Bethesda Research Laboratories, USA), the molecular length of the fragments being 1353 bp, 1078 bp, 872 bp, 603 bp, 310 bp, 281 bp, 271 bp, 234 bp, 194 bp, 118 bp and 72 bp in the order of large molecular length.

As mentioned above, the restriction sites of the plasmid pAG1 can be determined by digesting the plasmid pAG1 with various kinds of restriction enzymes, electrophoresing the resultant DNA fragments on an agarose gel and on a polyacrylamide gel and analyzing the obtained results. Thus, there is obtained a restriction endonuclease cleavage map of the plasmid pAG1 as is shown in FIG. 1.

As mentioned above, the plasmid pAG1 is available from the microorganism *Corynebacterium melassecola* 22243 deposited with FRI under the accession number FERM BP-560. The *Corynebacterium melassecola* 22243 is a novel strain isolated from soil. The microbiological properties of the strain and the characteristics for determining the biotype of the strain are as follows.

(1) Microscopic characteristics:

Usually, the stain is a bacillus having a size of 0.5 to 1.0 μm × 0.8 to 2.0 μm. The cells of the strain are multiplied by snapping division and show angular and palisade (picket fence) arrangements and pleomorphism. The strain is Gram-positive and non-motile. No sporulation is observed.

(2) Color and cultural characteristics:

Colonies formed on a bouillon agar plate are of circle with a distinct edge, opaque and lustrous. The color is yellowish milky white. On a bouillon agar slant, the strain grows well along an inoculated line and does not give an offensive smell. Any coloration of the bouillon agar is not observed. In the case of agar stab culture, the strain grows well at the uppermost part of the agar medium. In a liquid bouillon medium, the medium becomes turbid homogeneously and a ring is formed on the surface of the medium.

(3) Physiological characteristics:

a. Temperature: Growth is observed at a temperature of 25° C. to 37° C.

b. pH value: The strain can grow at pH 6 to pH 9.

c. Heat resistance: resistant at about 55° C. for about 15 minutes in a medium containing 10% skim milk.

d. Aerobic bacterium.

e. Gelatin liquefaction: negative.

f. The color of litmus milk: not changed.

g. Indole production: negative.

h. Voges-Proskauer test: negative.

i. Methyl red test: positive.

j. Hydrogen sulfide production: negative.

k. Nitrate reduction: positive l. Citric acid utilization: negative.

m. Starch liquefaction: negative n. Urease production: positive.

o. Catalase production: positive.

p. Acid production from various carbohydrates:

Positive from glucose, fructose, sucrose, maltose and mannose. Negative from mannitol, xylose, arabinose, raffinose and lactose.

q. Biotin is required for growth.

r. A remarkable amount of L-glutamic acid is produced in a medium containing a limited amount of biotin or in a surfactant-added medium containing a high amount of biotin.

With respect to the strain 22243 having the above-mentioned microbiological properties, the taxonomical placement thereof was determined with reference to "Bergey's Manual of Determinative Bacteriology, Eighth Edition" and Japanese Patent No. 576690 and making a comparison with *Corynebacterium melassecola* ATCC 17965 as a type culture. As a result, it has been found that the characteristics of the strain 22243 are quite similar to those of *Corynebacterium melassecola*. Therefore, the strain 22243 is identified as *Corynebacterium melassecola* and termed *Corynebacterium melassecola* 22243. As mentioned above, the mycrobiological characteristics of *Corynebacterium melassecola* 22243 is well in agreement with those of *Corynebacterium melassecola*. However, *Corynebacterium melassecola* 22243 is characterized by the possession of the plasmid pAG1 containing a gene for tetracycline resistance. It has been confirmed by the later-mentioned Referential Examples 1 and 2 that a gene for tetracycline resistance is contained in the plasmid pAG1.

The plasmid pAG1 can be easily isolated and purified by a process which comprises subjecting the above-mentioned strain to treatment with lysozyme-SDS to obtain a lysed cell solution, subjecting the obtained lysed cell solution to treatment with phenolchloroform, subjecting the thus obtained solution to ethanol precipitation and subjecting the obtained precipitates to cesium chloride density-gradient centrifugation in which ethidium bromide is used (see T. Maniatis, E. F. Fritsch, J. Sanbrook: Molecular Cloning A Laboratory Manual, Cold Spring Harbor Laboratory, Cold Spring Harbor N.Y. 1982). As a result, the plasmid pAG1 is obtained in substantially pure form.

The thus obtained plasmid pAG1 has a gene for replication in the cell of a glutamic acid-producing coryneform bacterium in addition to a gene for tetracycline resistance. The gene for replication means a gene which is necessary for a plasmid to be replicated in a cell for multiplication. Therefore, when a glutamic acid-producing coryneform bacterium is transformed with the plasmid pAG1, the plasmid pAG1 is multiplied in the cell of the bacterium and confers tetracycline resistance on the bacterium.

The plasmid pAG1 may be modified as far as the gene for tetracycline resistance and the gene for replication are not injured. For example, part of the plasmid pAG1 may be deleted while retaining the gene for tetracycline resistance and the gene for replication in the plasmid to obtain a deletion derivative of the plasmid pAG1. The partial deletion of the plasmid may be effected by digesting the plasmid pAG1 with one or more of restriction enzymes and annealing the resulting digests.

As specific examples of such a deletion derivative, there may be mentioned plasmids pAG12, pAG14, pAG31 and pAG32.

The plasmids paG12, pAG14, pAG31 and pAG32 has a molecular length of about 10.7 kb, about 10.7 kb, about 8.4 kb and about 7.3 kb, respectively. The restriction endonuclease cleavage maps of the plasmids pAG12, pAG14, pAG31 and pAG32 are shown in FIGS. 3, 4, 5 and 6, respectively.

Hereinafter, detailed explanation will be made of the preparation of each of the above-mentioned plasmids of the present invention.

Plasmids pAG12 and pAG14

The plasmids pAG12 and pAG14 may be prepared from the plasmid pAG1. As mentioned above, the plasmid pAG1 may be easily isolated and purified by a process which comprises subjecting a culture of the microorganism Corynebacterium melassecola 22243 to treatment with lysozyme-SDS, subjecting the obtained lysed cell solution to treatment with phenol-chloroform, subjecting the obtained solution to treatment with ethanol precipitation and finally subjecting the obtained precipitates to ethidium bromide-containing cesium chloride density-gradient centrifugation.

From the thus obtained plasmid pAG1 which has eight EcoRI sites, the plasmids pAG12 and pAG14 may be prepared by deleting part of the plasmid pAG1 using EcoRI while retaining a gene for tetracycline resistance and a gene for replication in the plasmid as follows. First, the plasmid pAG1 is completely digested with a restriction enzyme EcoRI to obtain a linear DNA fragment, and then the thus obtained linear DNA fragment is treated with T4 phage DNA ligase to form a circular DNA. With the circular DNA (plasmid), cells of a glutamic acid-producing coryneform bacterium are transformed, and the transformed cells which have a plasmid containing a gene for tetracycline resistance are selected by the criterion of tetracycline resistance. Then, the plasmids contained in the selected cells are analyzed to confirm that the plasmid contains the desired gene for tetracycline resistance and gene for replication. The transformation of the cells with the above-mentioned circular DNA may be performed according to the customary transformation method for *Bacillus subtilis* etc. in which a protoplast is employed as a host cell.

Figure 3:
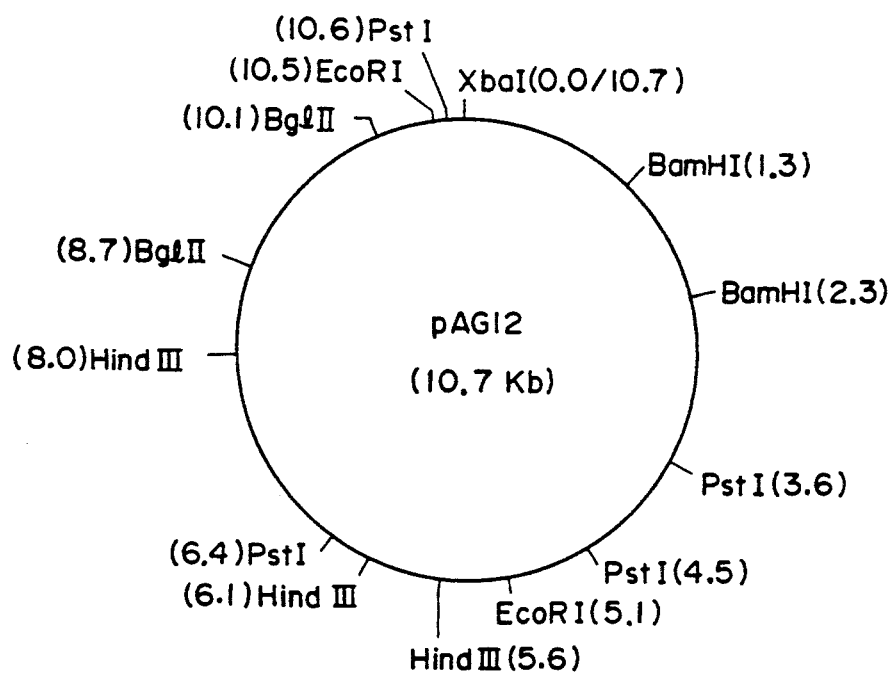
FIG. 3 illustrates the restriction endonuclease cleavage map of a plasmid pAG12 of the present invention.
Figure 4:
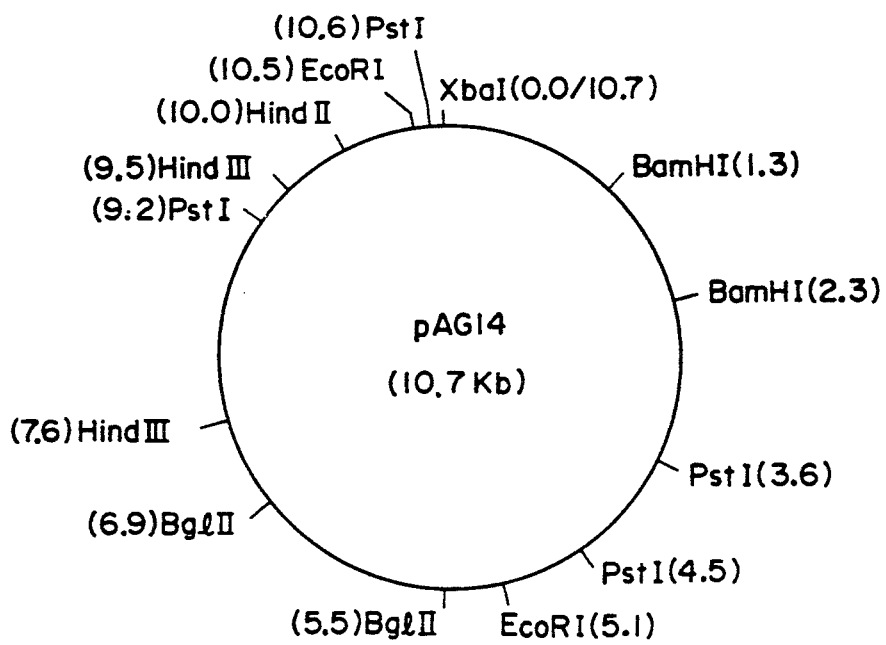
FIG. 4 illustrates the restriction endonuclease cleavage map of a plasmid pAG14 of the present invention.

The plasmid contained in the thus obtained transformed strain may be isolated from the culture of the strain and purified according to the method as mentioned above. The structure of the plasmid may be determined by analyzing DNA fragments formed by digesting the plasmid with various restriction enzymes and subjecting the resulting digests to agarose gel electrophoresis and, then, to polyacrylamide gel electrophoresis. As a result, it is found that two kinds of plasmids are obtained. The plasmids isolated from the transformed strains are designated pAG12 and pAG14, respectively. FIGS. 3 and 4 illustrate the restriction endonuclease cleavage maps of the plasmids pAG12 and pAG14, respectively. The plasmid pAG12 is a recombinant DNA consisting of two EcoRI fragments derived from plasmid pAG1 which are ligated each other in such a way that the orientation of the first EcoRI fragment is opposite to the orientation of the second one, and the plasmid pAG14 is a recombinant DNA consisting of two EcoRI fragments derived from plasmid pAG1 which are ligated each other in such a way that the orientation of the first EcoRI fragment is the same as the orientation of the second one. Both the plasmids have one XbaI site. Both the plasmids contain the gene for tetracycline resistance, and therefore, when any of the plasmids is used for transformation of a glutamic acid-producing coryneform bacterium, the transformed cells can be easily selected by the criterion of the tetracycline resistance.

Plasmids pAG31 and pAG32

The plasmids pAG31 and pAG32 may be prepared by deleting part of the plasmid pAG12 while retaining a gene for tetracycline resistance and a gene for replication which are derived from a glutamic acid-producing coryneform bacterium in accordance with the following process. The plasmid pAG12 which has been obtained in substantially the same manner as mentioned above is partially digested with restriction enzyme EcoRI [T. I. TIKCHONENKO, E. V. KARAMOV, B. A. ZAVIZON and B. S. NARODITSKY: Gene, 4, 195-212 (1978)] to obtain a linear DNA fragment. Then, the thus obtained linear DNA fragment is treated with T4 phage DNA ligase to obtain a circular plasmid. With the thus obtained plasmid, a glutamic acid-producing coryneform bacterium is transformed, and the transformed cells which have a plasmid containing a gene for tetracycline resistance are selected by the criterion of the tetracycline resistance. Then, the plasmid contained in the selected cells are analyzed to confirm that the plasmids contain the desired gene for tetracycline resistance and gene necessary for replication.

Figure 5:
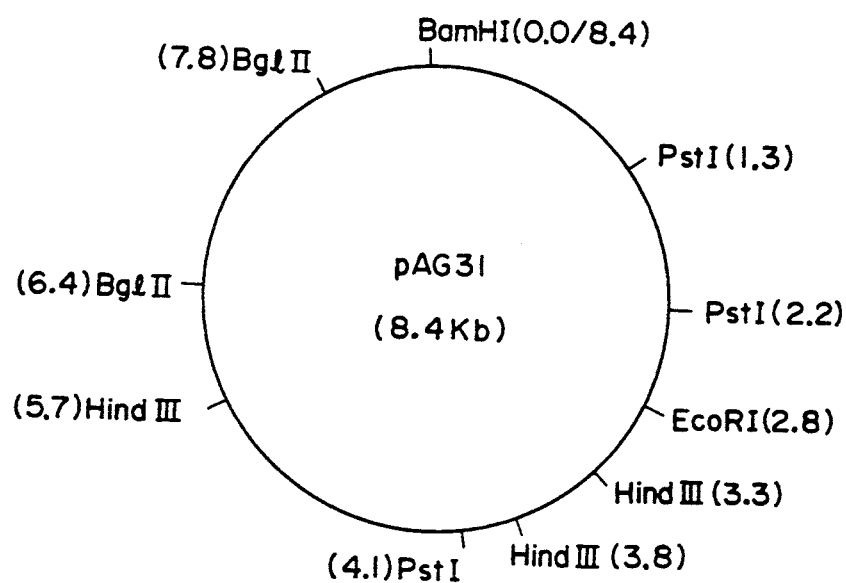
FIG. 5 illustrates the restriction endonuclease cleavage map of a plasmid pAG31 of the present invention.
Figure 6:
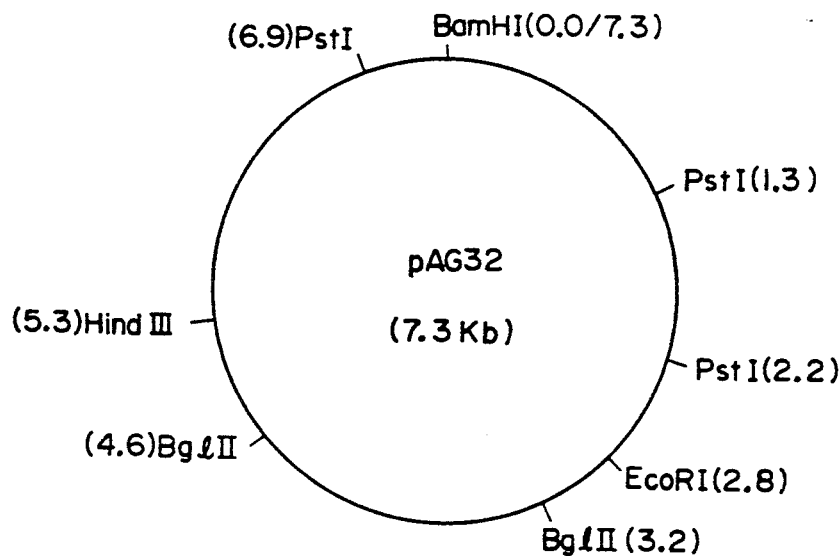
FIG. 6 illustrates the restriction endonuclease cleavage map of a plasmid pAG32 of the present invention.

The thus obtained plasmid contained in the transformed cells may be isolated from culture of the cells in substantially same manner as described with respect to the plasmids pAG12 and pAG14. The structure of the plasmid may be determined by analyzing DNA fragments formed by digesting with various restriction enzymes and subjecting the resulting digests to agarose gel electrophoresis and, then, to polyacrylamide gel electrophoresis. As a result, it is found that two kinds of plasmid are obtained. The plasmids isolated from the transformed cells are designated pAG31 and pAG32, respectively. FIGS. 5 and 6 illustrate the restriction endonuclease cleavage maps of the plasmids pAG31 and pAG32, respectively. The plasmid pAG31 is a recombinant plasmid consisting of two partially deleted EcoRI fragments derived from the plasmid pAG12 which are ligated each other in such a way that the orientation of the first partially deleted EcoRI fragment is the same as the orientation of the second one. The plasmid pAG32 is a recombinant plasmid consisting of two partially deleted EcoRI fragments derived from the plasmid pAG12 which are ligated each other in such a way that the orientation of the first EcoRI fragment is opposite to the orientation of the second one. The plasmid pAG31 has one BamHI site and one EcoRI site. The plasmid pAG32 has one BamHI site, one EcoRI site and one HindIII site. Since both the plasmids, namely pAG31 and pAG32, have one restriction site to be cleaved by EcoRI widely employed in the art, the insertion of DNA fragments containing a gene coding for a peptide desired for the production of an intended amino acid into the plasmid pAG31 or pAG32 is easily effected using the EcoRI site as an insertion site. Further, since the gene for tetracycline resistance may be utilized as a marker in both the plasmids, the cloning of a DNA fragment containing the gene for the above-mentioned desired peptide may be effected with high efficiency using a host-vector system comprising a glutamic acid-producing coryneform bacterium and either of the plasmids.

All the above-mentioned plasmids are derived from *Corynebacterium melassecola* 22243 and, therefore, all the plasmids are naturally suitable for transforming the above-mentioned strain. These plasmids may also be used for transforming glutamic acid-producing coryneform bacteria of the kind other than *Corynebacterium melassecola* 22243. However, from the standpoint of the stability and replicability in a cell, with respect to glutamic acid-producing coryneform bacteria of the kind other than *Corynebacterium melassecola* 22243, those plasmids respectively derived from the bacteria may, of course, be more suitably used as vectors for transforming the respective bacteria. In this case also, a DNA fragment containing a gene for tetracycline resistance derived from a glutamic acid-producing coryneform bacterium may advantageously be inserted into the plasmids derived from the bacteria of the kind other than *Corynebacterium melassecola* 22243 so that the gene for tetracycline resistance may be utilized as a marker. Further, with respect to glutamic acid-producing coryneform bacteria of the kind other than *Corynebacterium melassecola* 22243, any plasmid compatible with each of the bacteria may also be suitably used as a vector for transforming each bacterium. In this case also, a DNA fragment containing a gene for tetracycline resistance derived from a glutamic acid-producing coryneform bacterium may advantageously be inserted into the plasmid compatible with each bacterium of the kind other than *Corynebacterium melassecola* 22243 so that the gene for tetracycline resistance may be utilized as a marker. Thus, according to the present invention, there is provided a plasmid comprising a first DNA fragment containing a gene for tetracycline resistance derived from a glutamic acid-producing coryneform bacterium and a second DNA fragment containing a gene for replication in a cell of a glutamic acid-producing coryneform bacterium, said first DNA fragment being directly or indirectly ligated to said second DNA fragment.

As the first DNA fragment containing a gene for tetracycline resistance, there may be mentioned, for example, the DNA fragment derived from the plasmid pAG1 and the deletion derivatives thereof as mentioned above. Specific examples of such DNA fragments are as follows.

(1) a DNA fragment having a molecular length of about 3.2 kb and having one sticky end formed by BamHI cleavage and the other sticky end formed by BglII cleavage, and which has the following restriction sites:
 a SalI site, a first PstI site, a second PstI site and an EcoRI site which are respectively located about 0.7 kb, about 1.3 kb, about 2.2 kb and about 2.8 kb from said sticky end formed by BamHI cleavage;

(2) a DNA fragment having a molecular length of about 2.8 kb and having one sticky end formed by BamHI cleavage and the other sticky end formed by EcoRI cleavage, and which has the following restriction sites:
 a SalI site, a first PstI site and a second PstI site which are respectively located about 0.7 kb, about 1.3 kb and about 2.2 kb from said sticky end formed by BamHI cleavage;

(3) a DNA fragment having a molecular length of about 2.5 kb and having one sticky end formed by BglII cleavage and the other sticky end formed by SalI cleavage, and which has the following restriction sites:
 a first PstI site, a second PstI site and an EcoRI site which are respectively located about 0.6 kb, about 1.5 kb and about 2.1 kb from said sticky end formed by SalI cleavage; and (4) a DNA fragment having a molecular length of about 2.1 kb and having one sticky end formed by EcoRI cleavage and the other sticky end formed by SalI cleavage, and which has the following restriction sites:
 a first PstI site and a second PstI site which are respectively located about 0.6 kb and about 1.5 kb from said sticky end formed by SalI cleavage.

Figure 2:
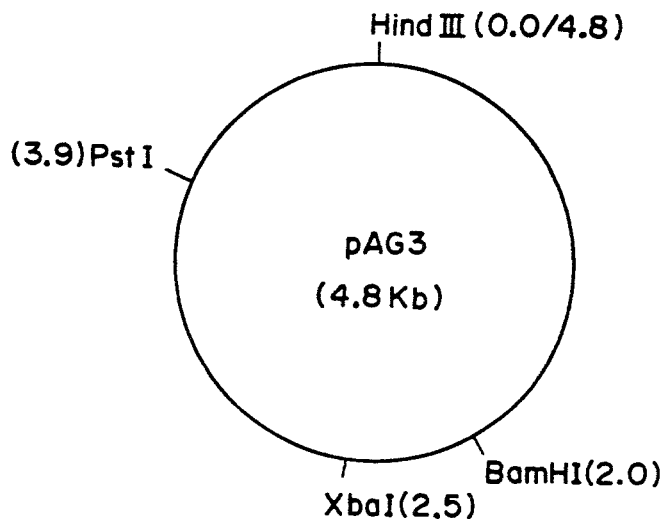
FIG. 2 illustrates the restriction endonuclease cleavage map of a plasmid pAG3 to be used in the present invention.

As the second DNA fragment, there may be employed any DNA fragments derived from a plasmid of a glutamic acid-producing coryneform bacterium. As such a DNA fragment, there may be mentioned, for example, a DNA fragment derived from a plasmid pAG3. The plasmid pAG3 is obtainable from the *Corynebacterium melassecola* 22220 deposited with the FRI under the accession number FERM BP-559, and has a molecular length of about 4.8 kb and a restriction endonuclease cleavage map as shown in FIG. 2. The microorganism *Corynebacterium melassecola* 22220 is a novel strain isolated from soil. The microbiological properties of the strain and the characteristics for determining the biotype of the strain are as follows.

(1) Microscopic characteristics:
Usually, the strain is a bacillus having a size of 0.5 to 1.0 $\mu$m $\times$ 0.8 to 2.0 $\mu$m. The cells of the strain are multiplied by snapping division and show angular and palisade (picket fence) arrangements and pleomorphism. The strain is Gram-positive and non-motile. No sporulation is observed.

(2) Color and cultural characteristics:
Colonies formed on a bouillon agar plate are of circle with a distinct edge, opaque and slightly lustrous. The color is yellow. On a bouillon agar slant, the strain grows well along an inoculated line and does not give an offensive smell. No coloration of the bouillon agar is observed. In the case of agar stab culture, the strain grows well at the uppermost part of the agar medium. In the case of a liquid bouillon medium, the medium becomes turbid homogeneously and a ring is formed on the surface of the medium.

(3) Physiological characteristics:
 a. Temperature: Growth is observed at a temperature of 25° C. to 37° C.
 b. pH value: The strain can grow at pH 6 to pH 9.
 c. Heat resistance: resistant at about 55° C. for about 15 minutes in a medium containing 10% skim milk.
 d. Aerobic bacterium.
 e. Gelatin liquefaction: negative.
 f. The color of litmus milk: not changed.
 g. Indole production: negative.
 h. Voges-Proskauer test: negative.
 i. Hydrogen sulfide production: negative.
 j. Methyl red test: positive.
 k. Nitrate reduction: positive.
 l. Citric acid utilization: negative.
 m. Starch liquefaction: negative
 n. Urease production: positive.
 o. Catalase production: positive.
 p. Acid production from various carbohydrates:
Positive from glucose, fructose, sucrose, maltose and mannose. Negative from mannitol, xylose, arabinose, raffinose and lactose.
 q. Biotin is required for growth.
 r. A remarkable amount of L-glutamic acid is produced in a medium containing a limited amount of biotin or in a surfactant-added medium containing a high amount of biotin.

With respect to the strain 22220 having the above-mentioned microbiological properties, the taxonomical placement thereof was determined with reference to "Bergey's Manual of Determinative Bacteriology, Eighth Edition" and Japanese Patent No. 576690 and making a comparison with *Corynebacterium melassecola* ATCC 17965 as a type culture. As a result, it has been found that the characteristics of the strain 22220 are quite similar to those of *Corynebacterium melassecola*. Therefore, the strain 22220 is identified as *Corynebacterium melassecola* and termed *Corynebacterium melassecola* 22220.

The restriction sites of the plasmid pAG3 can be determined in substantially the same manner as described with respect to the determination of restriction sites of the plasmid pAG1. The thus obtained restriction endonuclease cleavage map of the plasmid pAG3 is shown in FIG. 2.

The first DNA fragment may be directly ligated to the second DNA fragment. Alternatively, the first DNA fragment may be indirectly ligated to the second DNA fragment through another kind of a DNA fragment.

Figure 7:
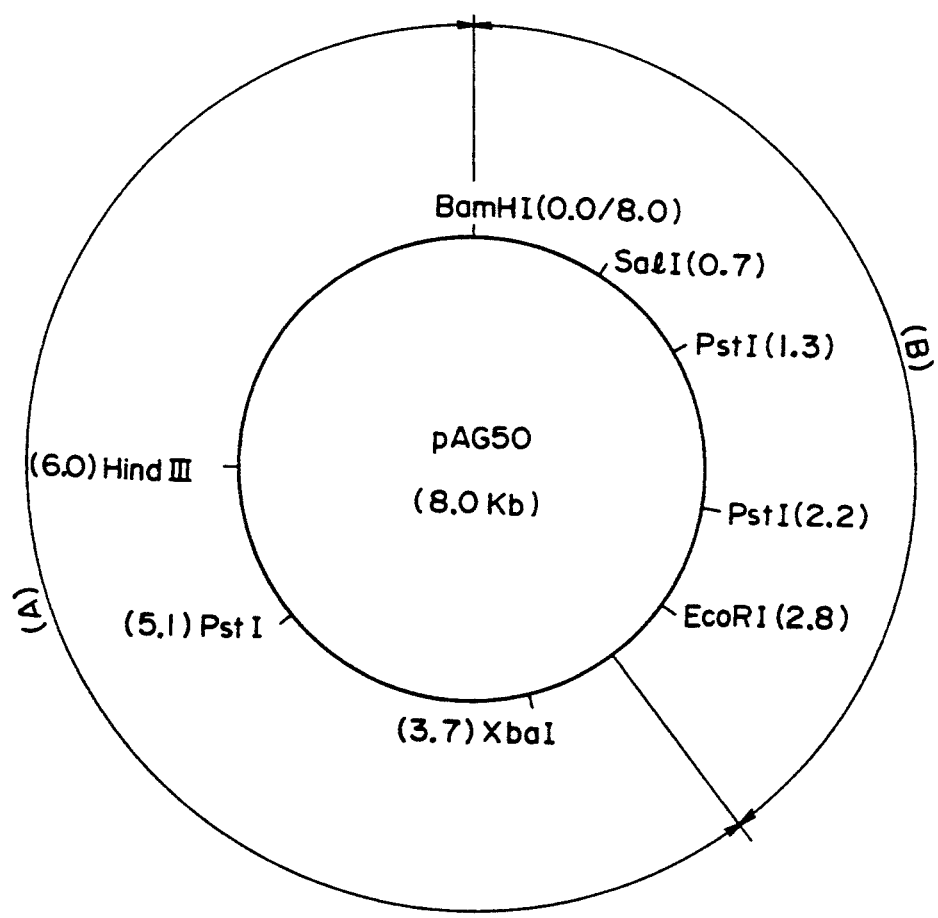
FIG. 7 illustrates the restriction endonuclease cleavage map of a plasmid pAG50 of the present invention.

As the plasmid comprising a first DNA fragment and a second DNA fragment there may be mentioned, for example, a plasmid pAG50. The plasmid pAG50 comprises as the first DNA fragment the DNA fragment (1) as mentioned above and as the second DNA fragment a BamHI cleaved fragment of the plasmid pAG3. In the plasmid pAG50, the first DNA fragment is directly ligated to the second DNA fragment. The plasmid pAG50 has a molecular length of about 8.0 kb and a restriction endonuclease cleavage map as shown in FIG. 7. The plasmid pAG50 may be prepared by inserting a BamHI-BglII fragment of the plasmid pAG14 mentioned above containing a gene for tetracycline resistance into the only one BamHI site of the plasmid pAG3 by the following process.

First, BamHI fragments of the plasmid pAG3 are reacted with BamHI-BglII fragments of the plasmid pAG14 containing a gene for tetracycline resistance in the presence of T4 phage DNA ligase to obtain a circular DNA (plasmid). With the thus transformed plasmid, a glutamic acid-producing coryneform bacterium is transformed and a transformed bacterium is selected by the criterion of the tetracycline resistance. Then, plasmids contained in the thus obtained transformed bacterium are isolated to obtain the plasmid pAG50. The plasmid pAG50 is analyzed in substantially the same manner as mentioned before to determine the restriction sites thereof.

The above-mentioned plasmids of the present invention may be modified by changing the base sequence of at least one restriction site of the plasmid so that the restriction enzyme effective for cleaving the restriction site is changed to a different kind of restriction enzyme, while retaining the gene for tetracycline resistance and the gene for replication.

Further, according to the present invention, there is provided a DNA fragment containing a gene for tetracycline resistance derived from a glutamic acid-producing coryneform bacterium. Such a DNA fragment may, as mentioned above, be used as the first DNA fragment of the above-mentioned plasmid comprising a first DNA fragment and a second DNA fragment. The DNA fragment of the present invention may be obtained from the plasmids containing a gene for tetracycline resistance derived from a glutamic acid-producing coryneform bacterium by a process which comprises cleaving the plasmid using restriction enzymes to obtain DNA fragments and isolating a DNA fragment containing a gene for tetracycline resistance from the DNA fragments.

The DNA fragment containing a gene for tetracycline resistance derived from a glutamic acid-producing coryneform bacterium as mentioned above may be easily modified by changing the base sequence of at least one restriction site of the DNA fragment so that the restriction enzyme effective for cleaving the restriction site is changed to a different kind of restriction enzyme, while retaining the gene for tetracycline resistance. The DNA fragment may also be changed at least at its one end with respect to base sequence so that the end of the DNA fragment may be adapted to the base sequence of a cleaved portion of a vector, which cleaved portion is to be ligated to the end of the DNA fragment.

Further, according to the present invention, there is provided a microorganism which comprises a coryneform bacterium and a DNA fragment containing a gene for tetracycline resistance derived from a glutamic acid-producing coryneform bacterium, said DNA fragment being contained in said coryneform bacterium.

Examples of the coryneform bacterium as the host include bacteria belonging to genera Corynebacterium, Brevibacterium and Microbacterium. Among them, glutamic acid-producing coryneform bacteria are preferred. As the glutamic acid-producing coryneform bacterium, there may be mentioned a plasmid cured strain of the *Corynebacterium melassecola* 22243, *Corynebacterium melassecola* 801 deposited with the FRI under the accession number FERM BP-558, etc.

As the DNA fragment to be contained in the coryneform bacteria, the DNA fragments as mentioned above may be employed.

As the microorganism of the present invention, there may be mentioned, for example, a microorganism *Corynebacterium melassecola* 22243 mentioned above. The *Corynebacterium melassecola* 22243 is, as mentioned above, deposited with the FRI under the accession number FERM BP-560, and the culture of the microorganism is available from the FRI in biologically pure form.

As the microorganism of the present invention, there may also be mentioned, for example, a microorganism which comprises a microorganism *Corynebacterium melassecola* 801 deposited with the FRI under the accession number FERM BP-558 as the coryneform bacterium and the DNA fragment (1) mentioned before as the DNA fragment containing a gene for tetracycline resistance, said DNA fragment (1) being in such a form that it is ligated to the plasmid pAG3 to form the plasmid pAG50. The microorganism is obtained by transforming the Corynebacterium melassecola 801 with the plasmid pAG50. The *Corynebacterium melassecola* 801 is isolated from soil and contains no plasmids. The microbiological characteristics of the strain and the characteristics for determining the biotype of strain are as follows.

(1) Microscopic characteristics:

Usually, the strain is a bacillus having a size of 0.5 to 1.0 μm×0.8 to 2.0 μm and different in size. The cells of the strain are multiplied by snapping division and show angular and palisade (picket fence) arrangements and pleomorphism. The strain is Gram-positive and non-motile. No sporulation is observed.

(2) Color and cultural characteristics:

Colonies formed on a bouillon agar plate are of circle with a distinct edge, opaque and lustrous. The color is yellow. On a bouillon agar slant, the strain grows well along an inoculated line and does not give an offensive smell. No coloration of the bouillon agar is observed. In the case of agar stab culture, the strain grows well at the uppermost part of the agar medium. In the case of a liquid bouillon medium, the medium becomes turbid homogeneously and a ring is formed on the surface of the medium.

(3) Physiological characteristics:

a. Temperature: Growth is observed at a temperature of 25° C. to 37° C.

b. pH value: The strain can grow at pH 6 to pH9.

c. Heat resistance: resistant at about 55 C for about 15 minutes in a medium containing 10% skim milk.

d. Aerobic bacterium.

e. Gelatin liquefaction: negative.

f. The color of litmus milk: not changed.

g. Indole production: negative.

h. Voges-Proskauer test: negative.
i. Hydrogen sulfide production: negative.
j. Methyl red test: positive.
k. Nitrate reduction: negative.
l. Citric acid utilization: negative.
m. Starch liquefaction: negative.
n. Urease production: positive.
o. Catalase production: positive.
p. Acid production from various carbohydrates:
Positive from glucose, fructose, sucrose, maltose and mannose. Negative from mannitol, xylose, arabinose, raffinose and lactose.
q. Biotin is required for growth.
r. A remarkable amount of L-glutamic acid is produced in a medium containing a limited amount of biotin or in a surfactant-added medium containing a high amount of biotin.

With respect to the strain 801 having the abovementioned microbiological properties, the taxonomical placement thereof was determined with reference to "Bergey's Manual of Determinative Bacteriology, Eighth Edition" and Japanese Patent No. 576690 and making a comparison with *Corynebacterium malassecola* ATCC 17965 as a type culture. As a result, it has been found that the characteristics of the strain 801 are quite the same as those of *Corynebacterium melassecola*. Therefore, the strain 801 is identified as *Corynebacterium melassecola* and termed *Corynebacterium melassecola* 801. The *Corynebacterium melassecola* 801 is deposited with the FRI under the accession number FERM BP-558 and is available from the FRI.

The plasmid and the DNA fragment of the present invention have the following advantages.

When a glutamic acid-producing coryneform bacterium, the growth of which is inhibited in a medium containing tetracycline even at a concentration of as low as about 1 µg/ml, is transformed with the plasmid of the present invention, the bacterium becomes tetracycline resistant, that is, the transformed bacterium can grow in a medium containing tetracycline at a concentration as high as 10 µg/ml. Therefore, a transformed bacterium is easily and effectively selected and separated from an untransformed bacterium by adding tetracycline to the culture medium to have a tetracycline concentration of 10 µg/ml. Further, when a conventionally known selective marker derived from a glutamic acid-producing coryneform bacterium, i.e., a gene for streptomycin and spectinomycin resistance is inserted into the present plasmid containing a gene for tetracycline resistance and the resultant is used as an expression vector for a gene coding for a peptide desired for the production of the intended amino acid in such a manner that the gene coding for the desired peptide is inserted into the gene for tetracycline resistance, the plasmid containing the gene coding for the desired peptide can be easily and effectively selected utilizing the inactivation of the selective marker due to the insertion of the gene coding for the desired peptide into the selective marker as explained before.

When the DNA fragment of the present invention containing a gene for tetracycline resistance derived from a glutamic acid-producing coryneform bacterium is inserted into a plasmid derived from or compatible with a glutamic acid-producing coryneform bacterium, there is obtained a plasmid which has as a selective marker a gene for tetracycline resistance and can advantageously be used as a vector in the cell of a glutamic acid-producing coryneform bacterium as a host with an increased copy number and stability.

Further, the microorganism of the present invention containing a gene for tetracycline resistance may be advantageously used as a stable, effective host-vector system for genetic recombination of a glutamic acid-producing coryneform bacterium.

As is apparent from the foregoing, by the use of the plasmid, DNA fragment or microorganism of the present invention, the breeding of a glutamic acid-producing coryneform bacterium can be easily and efficiently effected by recombinant DNA technique.

PREFERRED EMBODIMENT OF THE INVENTION

The present invention will be illustrated in more detail with reference to the following Referential Examples and Examples, which should not be construed to be limiting the scope of the present invention.

In Example 1, The existence of gene for tetracycline resistance in the plasmid pAG1 of the present invention is apparent from the fact that the strain obtained from the *Corynebacterium melassecola* 22243 (deposited with the Fermentation Research Institute under the accession number FERM BP-560) by curing the plasmid pAG1 contained therein is sensitive to tetracycline, and from the fact that the strain becomes tetracycline resistant when the plasmid pAG1 is incorporated in the plasmid-cured strain. These facts will be illustrated below by way of Referential Examples 1 and 2. With respect to the plasmids of the present invention other than the plasmid pAG1 also, the existence of a gene for a tetracycline resistance in each of the plasmids is confirmed by the experiment in which substantially the same procedures as in Referential Examples 1 and 2 are repeated except that each of the plasmids is used instead of the plasmid pAG1. Further, with respect to the DNA fragment of the present invention, the existence of a gene for tetracycline resistance in the DNA fragment is confirmed by the experiment in which substantially the same procedures as in Referential Examples 1 and 2 are repeated except that the DNA fragment is inserted into a plasmid containing no gene for tetracycline resistance and the resulting plasmid is used instead of the plasmid pAG1.

REFERENTIAL EXAMPLE 1

Curing of plasmid pAG1 in *Corynebacterium melassecola* 22243 (deposited with the Fermentation Research Institute under the accession number FERM BP-560)

A loopful of *Corynebacterium melassecola* 22243 (deposited with the Fermentation Research Institute under the accession number FERM BP-560) was inoculated into 5 ml of LG medium as obtained by dissolving 10 g of tryptone, 5 g of yeast extract, 5 g of NaCl and 2 g of glucose in ion-exchanged and distilled water to make up a 1 l solution and adjusting the hydrogen ion concentration of the solution to pH 7.2, and cultured while shaking at 37° C. overnight. The cell culture was diluted with sterilized water, spread on LG agar medium as obtained by adding 1.5% of agar to the above-mentioned LG medium, and incubated at 32° C. for 2 days. 100 colonies were taken out from the resulting colonies, and inoculated into LG agar medium containing 10 µg/ml of tetracycline by replica-plating. The cell culture was incubated at 32° C. for 2 days, and then two colonies exhibiting a tetracycline sensitivity were isolated. From the colonies the plasmids contained therein were separated in substantially the same manner as will be described in Example 1 to be given later to check the existence of the plasmid pAG1. As a result, it was found that the two colonies exhibiting a tetracycline sensitivity did not contain the plasmid pAG1.

REFERENTIAL EXAMPLE 2

Transformation of plasmid-cured strain of *Corynebacterium melassecola* 22243 (deposited with the Fermentation Research Institute under the accession number FERM BP-560) with plasmid pAG1.

The plasmid-cured strain of *Corynebacterium melassecola* 22243 (deposited with the Fermentation Research Institute under the accession number FERM BP-560) as obtained in Referential Example 1 was cultured while shaking in a semi-synthetic medium (which is of the same kind as that in Example 1 to be given later) at 32° C. for 12 hours. From the cell culture 0.5 ml was taken out, inoculated into 50 ml of the same semi-synthetic medium as mentioned above, and incubated while shaking at 32° C. When the absorbance at 660 nm of the cell culture as measured by means of the spectrophotometer Model 228 manufactured and sold by Hitachi Ltd. became 0.2, penicillin G was added to the cell culture to a final concentration of 0.3 unit/ml. Thereafter, incubation of the cell culture was continued at 32° C. for 1.5 hours. From the resulting cell culture the cells were harvested, and suspended in 5 ml of R medium as obtained by dissolving 5 g of glucose, 10 g of Casamino acid, 10 g of yeast extract, 0.35 g of $K_2HPO_4$, 0.15 g of $KH_2PO_4$, 137 g of sucrose, 5.73 g of N-tris-(hydroxymethyl)methyl-2-aminoethanesulfonic acid (hereinafter referred to as TES), 0.95 g of $MgCl_2$ and 1.11 g of $CaCl_2$ in distilled water to obtain a 1 l solution and adjusting the hydrogen ion concentration of the solution to pH 7.2 by the use of NaOH. The number of normal cells of the suspension to be subjected to a lysozyme treatment was found to be $7.6 \times 10^8$ ml$^{-1}$ by (1) taking out an aliquot from the suspension, (2) diluting the aliquot with R medium, and (3) spreading the mixture on LG agar medium, followed by incubation at 32° C. for 2 days.

To 4.5 ml of the above-mentioned cell suspension was added 0.5 ml of R medium pre-sterilized with a millipore filter which contained lysozyme in a concentration of 3 mg/ml, and incubated while keeping still at 35° C. for 5 hours.

The resulting protoplast cells were harvested by 7,000 rpm (4,500 g) centrifugation at 5° C. for 7 min, and suspended in 5 ml of R medium. The same operations were repeated to obtain a protoplast cell suspension. The ratio of the number of cells forming a colony under a hypotonic condition which were present in the protoplast cell suspension to the above-mentioned number of normal cells subjected to the lysozyme treatment was determined by (1) taking out an aliquot from the protoplast cell suspension, (2) diluting the aliquot with sterilized water, (3) spreading the mixture on LG agar medium (hypotonic condition), (4) incubating the cell culture at 32° C. for 2 days, and (5) counting the number of formed colonies, followed by calculation of the above-mentioned ratio. Even if the incubation at (4) above was continued for more than 2 days, the number of formed colonies did not increase. The above-mentioned ratio was determined to be $1.3 \times 10^{-5}$. On the other hand, the ratio of the number of cells forming a colony under a hypertonic condition which were present in the protoplast cell suspension to the above-mentioned number of normal cells subjected to the lysozyme treatment was determined by (1) taking out another aliquot from the protoplast cell suspension, (2) diluting the aliquot with R medium, (3) inoculating the mixture into the regenerating medium (hypertonic condition) [the regenerating medium was a double-layer agar medium comprising a lower agar medium layer as obtained by adding polyvinyl pyrrolidone (hereinafter referred to as PVP) and agar in respective concentrations of 40 g/l and 15 g/l to R medium and, superimposed on the lower layer, an upper agar medium layer as obtained by adding PVP and agar in respective concentrations of 40 g/l and 6 g/l to R medium; and inoculation of the above-mentioned mixture was effected by mixing it with 3 ml of the upper agar medium layer before forming the double layer], (4) incubating the cell culture at 32° C. for 4 days, and (5) counting the number of formed colonies, followed by calculation of the above-mentioned ratio. Even if the incubation at (4) above is continued for more than 4 days, the number of formed colonies did not increase. The above-mentioned ratio was determined to be $2.4 \times 10^{-1}$.

Transformation was effected using the above-mentioned protoplast cell suspension as follows. 50 µl of a plasmid pAG1 solution containing 1.25 µg of DNA was mixed with 50 µl of a 2×TSMC solution containing 50 mM TES, 0.8M sucrose, 20 mM $MgCl_2$ and 60 mM $CaCl_2$ which solution was adjusted to pH 7.2 by the use of NaOH, and further with 0.5 ml of the above-mentioned protoplast cell solution. To the resulting mixture was added 1.5 ml of a PEG solution as prepared by dissolving a polyethylene glycol having a molecular weight of 6,000 in a TSMC solution containing 25 mM TES, 0.4M sucrose, 10 mM $MgCl_2$ and 30 mM $CaCl_2$, which solution was adjusted to pH 7.2 by the use of NaOH, to a final concentration of 40% (w/v). The suspension was gently mixed, and kept undisturbed for 2 min. Then, to the suspension was added 5 ml of an R-PVP solution as prepared by dissolving PVP in R medium to a final concentration of 40 g/l, and centrifuged at 4,000 rpm (1,800 g) for 10 min, followed by removal of the supernatant. These operations of adding the R-PVP solution and centrifuging were repeated to obtain a protoplast pellet. The protoplast pellet was gently suspended in 0.5 ml of the R-PVP solution, incubated at 30° C. for 3 hr, and diluted with the R-PVP solution. An aliquot was taken out from the suspension and inoculated into a medium as prepared by adding tetracycline to the above-mentioned regenerating medium to a final concentration of 10 µg/ml in order to find the number of tetracycline resistant transformants. Concurrently, another aliquot was taken out from the suspension and inoculated into the above-mentioned regenerating medium in order to find the number of colony-forming cells. The cell cultures were incubated at 32° C. for 4 days, and then the number of formed colonies was counted. Also, a control trial was effected in substantially the same manner as described above except that the plasmid pAG1 was not employed.

As a result, it was found that the ratio of the number of colony-forming cells after execution of the above-described transformation operations to the number of normal cells subjected to the lysozyme treatment was $1.8 \times 10^{-2}$, and that the ratio of the number of tetracycline resistant transformants to the number of normal cells subjected to the lysozyme treatment was $3.2 \times 10^{-4}$. It was also found that $10^5$ tetracycline resistant colonies were formed per µg of the added plasmid DNA. On the other hand, formation of any tetracycline resistant colony was not recognized in the control trial in which the plasmid pAG1 was not employed. Moreover, it was found that all of the 12 strains randomly chosen from the obtained tetracycline resistant transformants contained the plasmid pAG1 as a result of an isolation and analysis of plasmids which was conducted in substantially the same manner as will be described in Example 1 to be given later.

EXAMPLE 1

Isolation of a plasmid pAG1 from *Corynebacterium melassecola* 22243 (FERM BP-560)

The microorganism *Corynebacterium melassecola* 22243 was cultured in a semi-synthetic medium [a medium prepared by dissolving 10 g of $(NH_4)_2SO_4$, 3 g of urea, 1 g of $K_2HPO_4$, 50 mg of NaCl, 400 mg of $MgSO_4.7H_2O$, 2 mg of $MnSO_4.4-6H_2O$, 2 mg of $FeSO_4.4-6H_2O$, 20 g of glucose, 50 μg of biotin, 200 μg of thiamine hydrochloride and 1 g of yeast extract in ion-exchanged and distilled water so that the total volume becomes 1 liter, and adjusting at pH 7.2] at 32° C. overnight while shaking. 8 ml of the thus obtained culture was inoculated to 200 ml of the same semisynthetic medium, followed by culturing at 32° C. for 5 hours while shaking to obtain a culture of the microorganism.

From the culture, cells of the microorganism were collected and suspended in 10 ml of a lysozyme solution containing 50 mM glucose, 10 mM EDTA, 25 mM Tris(hydroxylmethyl)aminomethane (hereinafter often referred to as "Tris") and 10 mg/ml lysozyme (manufactured and sold by Sigma Chemical Company, U.S.A.), followed by incubation at 42° C. for 1 hour. To the suspension was added 20 ml of an alkali-SDS solution containing 0.2N NaOH and 1% (w/v) sodium dodecylsulfate (hereinafter often referred to as "SDS"). The mixture was stirred and, then allowed to stand in ice for 5 minutes. Then, to the mixture was added 15 ml of an ice-cooled potassium acetate solution (a mixture of 60 ml of 5M potassium acetate, 11.5 ml of acetic acid and 28.5 ml of ion-exchanged and distilled water). The mixture was stirred and allowed to stand in ice for 10 minutes to obtain a lysate. The whole lysate was transferred to a centrifuge tube and subjected to centrifugation at 12,000 rpm (13,000 g), 4° C. for 5 minutes, thereby to obtain a supernatant. The supernatant was subjected to extraction with an equi-volume of phenol-chloroform (1:1) and an aqueous phase was collected. To the aqueous layer was added 2-fold volume of ethanol, and the resulting mixture was stirred and allowed to stand at room temperature for 5 minutes. Then, the mixture was subjected to centrifugation at 10,000 rpm (11,000 g), 20° C. for 10 minutes, thereby to obtain precipitates. The precipitates were washed with 70% (v/v) ethanol, dried under reduced pressure and dissolved in 20 ml of a TE buffer containing 10 mM Tris and 1 mM EDTA (pH 7.5) in a centrifuge tube. To the resulting solution, 1.2 ml of 10 mg/ml aqueous ethidium bromide solution and 23.6 of cesium chloride were gently added and dissolved, followed by centrifugation at 40,000 rpm (100,000 g), 15° C. for 48 hours. After completion of the centrifugation, two bands were visualized under UV light. The lower band was taken out from the centrifuge tube through the side of the tube using a syringe to obtain a plasmid fraction. The thus obtained fraction was subjected to extraction with an equi-volume of isopropyl alcohol four times to obtain an extract. From the extract, ethidium bromide was removed and the resulting solution was dialyzed against the TE buffer to obtain 1 ml of a dialysate containing a plasmid at a concentration of 50 μg/ml.

From the dialysate, samples containing 0.5 μg of a plasmid were prepared, and they were mixed with the following restriction enzymes in a 20 μl of a suitable buffer and allowed to stand at 37° C. for 2 hours, thereby to digest the plasmid. As the restriction enzymes, there were used EcoRI, BamHI, HindIII and PstI (each manufactured and sold by Nippon Gene Co., Ltd., Japan) and XbaI (manufactured and sold by Bethesda Research Laboratories, U.S.A.). Each of the restriction enzymes was used in an amount of 10 units. The digestions were conducted using the restriction enzymes alone and in combination. The thus obtained digests were subjected to 1% (w/v) agarose gel electrophoresis and 4% (w/v) polyacrylamide gel electrophoresis according to the method of Maniatis et al [T. Maniatis, E. F. Fritsch, J. Sambrook; Molecular Cloning A Laboratory Manual, Cold Spring Harbor Laboratory, Cold Spring Harbor N.Y. p.150–185, 1982]. After completion of the electrophoresis, the gel was dipped in an ethidium bromide solution containing 1 μg/ml of ethidium bromide for 30 minutes to stain the gel. Then, the gel was irradiated with UV light to determine the number of bands which correspond to the number of DNA fragments obtained. The respective molecular lengths of the DNA fragments were determined by comparison of the respective distances of migration of the fragments in electrophoresis with those of the DNA fragments respectively having known molecular lengths. The molecular length of the plasmid was calculated by adding the molecular lengths of the respective DNA fragments. Further, based on the results obtained in the above analysis, the restriction endonuclease cleavage sites of the plasmid were determined. As mentioned above, the respective molecular lengths of the DNA fragments were determined by comparison of the respective distances of migration of the fragments in electrophoresis with those of the DNA fragments respectively having known molecular lengths. In determination of molecular lengths of 0.5 kb or more, there was employed 1% (w/v) agarose gel electrophoresis, and in determination of those of about 0.1 kb to less than 0.5 kb, there was employed 4% (w/v) polyacrylamide gel electrophoresis. As such a DNA fragment having a known molecular length, DNA fragments obtained by HindIII digestion of λ phage DNA (manufactured and sold by Nippon Gene Co., Ltd., Japan) were used in the case of the agarose gel electrophoresis, and DNA fragments obtained by HaeIII digestion of φ174 phage DNA (manufactured and sold by Bethesda Research Laboratories, U.S.A.) were used in the case of the polyacrylamide gel electrophoresis.

The result is shown in Table 1.

By the analysis of the DNA fragments obtained by digestion of the plasmid with various restriction enzymes, the restriction endonuclease cleavage map of the plasmid was determined and shown in FIG. 1. The plasmid was designated pAG1.

TABLE 1

| Restriction enzyme | EcoRI | PstI | HindIII |
|---|---|---|---|
| Number of restriction sites | 8 | 5 | 5 |
| Molecular length of DNA fragments obtained (kb) | 5.4 | 9.5 | 11.5 |
| | 5.3 | 4.9 | 3.9 |
| | 4.3 | 3.7 | 2.6 |
| | 2.0 | 1.4 | 1.9 |

TABLE 1-continued

| Restriction enzyme | EcoRI | PstI | HindIII |
|---|---|---|---|
| | 1.7 | 0.9 | 0.5 |
| | 0.7 | | |
| | 0.7 | | |
| | 0.3 | | |
| Total (kb) (molecular length of the plasmid) | 20.4 | 20.4 | 20.4 |

EXAMPLE 2

Preparation of Plasmids pAG12 and pAG14

Step 1. In vitro Recombination of Plasmid pAG1

To 0.5 μg of the plasmid pAG1 DNA prepared in Example 1 was added 10 units of the restriction enzyme EcoRI. The resulting mixture was reacted in 40 μl of a buffer containing 50 mM Tris-HCl (pH 7.4), 10 mM MgSO$_4$ and 100 mM NaCl at 37° C. for 2 hours. Then, the temperature was elevated to 70° C., and the mixture was heated at 70° C. for 10 minutes to terminate the reaction. 20 μl of the thus obtained reaction mixture was reacted ti 3 units of T4 phase DNA ligase (manufactured and sold by Nippon Gene Co., Ltd., Japan) in 50 μl of a buffer containing 50 mM Tris-HCl (pH 7.4), 10 mM MgCl$_2$, 10 mM dithiothreitol, 1 mM spermidine, 1 mM ATP and 1 mg/ml of BSA (bovine serum albumin) (manufactured and sold by Bethesda Research Laboratories, U.S.A.) at 15° C. overnight.

Step 2. Isolation of Plasmids pAG12 and pAG14

Using the recombinant DNA prepared from the plasmid pAG1 in Example 2 step 1, the plasmid-cured strain of *Corynebacterium melassecola* 22243 (deposited with the FIR under the accession number FERM BP-560) was transformed to obtain a tetracycline resistant strain. From the tetracycline resistant strain, plasmids were isolated in substantially the same manner as in Example 1 and analyzed. As a result, two plasmids pAG12 and pAG14 were obtained. The method is described below in detail.

Plasmid curing

A loopful of *Corynebacterium melassecola* 22243 (FERM BP-560) was inoculated into 5 ml of an LG medium (a medium prepared by dissolving 10 g of trypton, 5 g of yeast extract, 5 g of NaCl and 2 g of glucose in ion-exchanged and distilled water so that the total volume becomes 1 liter, and adjusting at pH 7.2) and cultured at 37° C. overnight while stirring. The thus obtained culture was diluted with a sterilized water. The diluted culture was then spread on an LG agar medium (a medium prepared by adding agar to the LB medium so that the agar concentration of the resulting medium becomes 1.5% by weight), followed by culturing at 32° C. for 2 days to form colonies. 100 colonies thus formed were transferred by replica-plating onto LG agar plate containing 10 μg/ml of tetracycline, followed by culturing at 32° C. for 2 days. Then, 2 tetracycline sensitive strains were selected. With respect to the thus selected two strains, the existence of the plasmid pAG1 in the strains was determined by the plasmid isolation method as described in Example 1. As a result, it was found that both the strains contained no plasmids, that is, the strains were a plasmid cured strain. One of the strains was used as a host in the following step.

Transformation

The plasmid-cured strain prepared in the above step was cultured in the semi-synthetic medium mentioned before at 32° C. for 12 hours while shaking. 0.5 ml of the thus obtained culture was inoculated into 50 ml of the same semi-synthetic medium and cultured at 32° C. while shaking. The optical density (OD) of the culture at 660 nm was monitored using a spectrophotometer Model 228 (manufactured and sold by Hitachi, Ltd., Japan). At the point of time when the OD became 0.2, penicillin G was added to the culture so that the penicillin concentration became 0.3 unit/ml. The resulting culture was incubated at 32° C. for 1.5 hours.

From the thus obtained culture, cells were collected and suspended in 5 ml of the R medium to obtain a cell suspension. To 4.5 ml of the cell suspension was added 0.5 ml of the R medium containing 3 mg/ml of lysozyme (sterilized using Millipore filter), followed by incubation at 35° C. for 5 hours, thereby to form protoplasts. The resulting culture was subjected to centrifugation at 7,000 rpm (4,500 g), 5° C. for 7 minutes to obtain the protoplasts. The thus obtained protoplasts were suspended in 5 ml of the R medium. The protoplast suspension was subjected to centrifugation in the same conditions as mentioned just above to obtain protoplasts. The protoplasts were suspended in 5 ml of the R medium to obtain a protoplast suspension.

To 0.5 ml of the protoplast suspension was added a mixture of 50 μl of the mixture obtained in Example 2 step 1 and 50 μl of 2×TSMC solution (an aqueous solution containing 50 mM TES, 0.8M sucrose, 20 mM MgCl$_2$ and 60 mM CaCl$_2$ and adjusted to pH 7.2 using NaOH). Then, to the resulting mixture was gently added the PEG solution, and allowed to stand at room temperature for 2 minutes. Then, to the mixture was added 5 ml of an R-PVP solution, followed by centrifugation at 4,000 rpm (1,800 g) for 10 minutes to form a supernatant and precipitates. The supernatant was removed. To the precipitates was added 5 ml of the R-PVP solution, followed by the centrifugation in the same conditions as mentioned just above to obtain protoplasts as the precipitates. The thus obtained protoplasts were gently suspended in 0.5 ml of R-PVP solution. The suspension was incubated at 30° C. for 3 hours and diluted with R-PVP solution to obtain a diluted suspension. The diluted suspension was mixed with 3 ml of the melted agar medium having the same composition as that of the upper agar medium layer of the regenerating medium containing 10 μg/ml of tetracycline in Example 1, and the resulting mixture was applied onto the lower agar medium layer. The resulting regenerating medium was incubated at 32° C. for 4 days to form tetracycline resistant strains. From the thus formed tetracycline resistant strains, 10 strains were optionally selected and grown in biologically pure form on the LG agar medium containing 10 μg/ml of tetracycline. From each of the strains, a plasmid was isolated in substantially the same manner as in Example 1. From the thus isolated plasmid, 0.5 μg samples were prepared, and they were digested with the following restriction enzymes in a 20 μl of a suitable buffer at 37° C. for 2 hours. As the restriction enzymes, there were used EcoRI, BamHI, HindIII, BglII and PstI (each manufactured and sold by Nippon Gene Co., Ltd. Japan) and XbaI (manufactured and sold by Bethesda Research Laboratories, U.S.A.). Each of the restriction enzymes was used in an amount of 10 units. The digestions were conducted using the restriction enzymes alone and in combination. The thus obtained digests were subjected to 1% (w/v) agarose gel electrophoresis and 4% (w/v)

polyacrylamide gel electrophoresis according to the method of Maniatis et al [T. Maniatis, E. F. Fritsch, J. Sambrook; Molecular Cloning A Laboratory Manual, Cold Spring Harbor Laboratory, Cold Spring Harbor N.Y. p.150-185, 1982]. After completion of the electrophoresis, the gel was dipped in an ethidium bromide solution containing 1 $\mu$g/ml of ethidium bromide for 30 minutes to stain the gel. Then, the gel was irradiated with UV light to determine the number of bands which correspond to the number of DNA fragments obtained. The respective molecular lengths of the DNA fragments were determined by comparison of the respective distances of migration of the fragments in electrophoresis with those of the DNA fragments respectively having known molecular lengths. The molecular length of the plasmid was calculated by adding the molecular lengths of the respective DNA fragments. Further, based on the results obtained in the above analysis, the restriction endonuclease cleavage sites of the plasmid were determined. As mentioned above, the respective molecular lengths of the DNA fragments were determined by comparison of the respective distances of migration of the fragments in electrophoresis with those of the DNA fragments respectively having known molecular lengths. In determination of molecular lengths of 0.5 kb or more, there was employed 1% (w/v) agarose gel electrophoresis, and in determination of those of about 0.1 kb to less than 0.5 kb, there was employed 4% (w/v) polyacrylamide gel electrophoresis. As such a DNA fragment having a known molecular length, DNA fragments obtained by HindIII digestion of $\lambda$ phage DNA (manufactured and sold by Nippon gene Co., Ltd., Japan) were used in the case of the agarose gel electrophoresis, and DNA fragments obtained by HaeIII digestion of $\phi$X174 phage DNA (manufactured and sold by Bethesda Research Laboratories, U.S.A.) were used in the case of the polyacrylamide gel electrophoresis. Based on the number and the molecular lengths of the DNA fragments, the molecular length and restriction sites of the plasmids were determined. As a result, it was found that two kinds of the plasmids were obtained. The two plasmids were designated pAG12 and pAG14, respectively. The restriction endonuclease cleavage maps of the plasmids pAG12 and pAG14 are shown in FIGS. 3 and 4, respectively.

In substantially the same manner as mentioned above, the plasmid-cured strain of *Corynebacterium melassecola* 22243 (deposited with the Fermentation Research Institute under the accession number FERM BP-560) was transformed using these plasmids to obtain a tetracycline resistant transformant. The restriction endonuclease cleavage map of each plasmid retained in the transformant was found to be the same as that of each plasmid incorporated in the above transformation.

EXAMPLE 3

Preparation of Plasmids pAG31 and pAG32

Step 1. In vitro Recombination of Plasmid pAG12

To 2 $\mu$g of the plasmid pAG12 DNA prepared in Example 2 step 2 was added 10 units of the restriction enzyme EcoRI. The resulting mixture was reacted in 80 $\mu$l of buffer containing 25 mM Tris-HCl (pH 8.6), 2 mM MgSO$_4$ and 40% (w/w) glycerol at a temperature of 37° C. for a period of 90 min. Then, the temperature was elevated to 70° C., and the mixture was heated at 70° C. for 10 min to terminate the reaction. Sodium acetate was added to a final concentration of 300 mM, followed by addition of a two-fold volume of ethanol. The mixture was stirred for a while, and kept still at $-30°$ C. for 3 hr. Thereafter, the mixture was subjected to centrifugation at 12,000 rpm (8900 g) for 10 min to obtain a DNA pellet. The thus obtained DNA was dried in vacuo, and reacted with 3 units of T4 phage DNA ligase in 50 $\mu$l of buffer containing 50 mM Tris-HCl (pH 7.4), 10 mM MgCl$_2$, 10 mM dithiothreitol, 1 mM spermidine, 1 mM ATP and 0.1 mg/ml BSA (bovine serum albumin) at a temperature of 15° C. overnight. The temperature was elevated to 70° C., and the mixture was heated at 70° C. for 10 min to terminate the reaction.

Step 1. Isolation of Plasmids pAG31 and pAG32

Using 50 $\mu$l of the ligase reaction mixture prepared in Example 3 step 1, the plasmid-cured strain of *Corynebacterium melassecola* 22243 (deposited with the Fermentation Research Institute under the accession number FERM BP-560) was transformed in substantially the same manner as in Example 2 to obtain a tetracycline resistant transformant. From the thus obtained transformant were separated plasmids, followed by analysis in substantially the same manner as in Example 2 step 2. As a result, two kinds of plasmids were found and designated pAG31 and pAG32. The restriction endonuclease cleavage maps of these plasmids are shown in FIGS. 5 and 6.

In substantially the same manner as mentioned above, the plasmid-cured strain of *Corynebacterium melassecola* 22243 (deposited with the Fermentation Research Institute under the accession number FERM BP-560) was transformed using each plasmid to obtain a tetracycline resistant transformant. The restriction endonuclase cleavage map of each plasmid retained in the transformant was found to be the same as that of each plasmid incorporated in the above transformation.

EXAMPLE 4

Preparation of Plasmid pAG50

The plasmid pAG14 DNA was cleaved using restriction enzymes BamHI and BglII to obtain a mixture of DNA fragments. The mixture was subjected to electrophoresis using an agarose gel to isolate a DNA fragment containing a gene for tetracycline resistance and having a molecular length of about 3.2 kb. Next, T4 phage DNA ligase was added to a mixture of the above DNA fragment and the fragment obtained by cleaving the plasmid pAG3 with restriction enzyme BamHI. Using the resultant ligase reaction mixture, *Corynebacterium melassecola* 801 deposited with the Fermentation Research Institute under the accession number FERM BP-558 was transformed to obtain a tetracycline resistant transformant. From the thus obtained transformant was separated plasmid pAG50 in accordance with the procedures as described below.

Step 1. Isolation of DNA Fragment Containing Gene for Tetracycline Resistance

To 20 $\mu$g of the plasmid pAG14 DNA obtained in Example 2 step 2 were added 100 units each of restriction enzymes BamHI and BglII. The resulting mixture was reacted in 100 $\mu$l of buffer containing 10 mM Tris-HCl (pH 7.4), 10 mM MgSO$_4$, 50 mM NaCl and 1 mM dithiothreitol at a temperature of 37° C. for a period of 2 hr. The digested plasmid was subjected to electrophoresis at 4° C. using a 1% agarose gel prepared from LMP Agarose (trade name for a product manufactured and sold by Bethesda Research Laboratories, U.S.A.) in substantially the same manner as in Example 2 step 2. The agarose gel was stained with ethiidium bromide and exposed to ultraviolet light irradiation, so that there were visually observed DNA fragments containing a gene for tetracycline resistance and having a molecular length of about 3.2 kb. The portion of the gel in which such DNA fragments were found was cut off. To the cut off gel was added TE buffer in an amount of three times the weight of the gel, and heated at 65° C. for 10 min to effect complete dissolution of the agarose gel. To the resulting solution was added an equivolume of phenol and stirred, followed by recovery of an aqueous phase. To the aqueous phase was added an equivolume of a 1:1 mixture of phenol and chloroform and stirred, followed by recovery of an aqueous phase. To the aqueous phase was added an equivolume of chloroform and stirred, followed by recovery of an aqueous phase. To the aqueous phase was added sodium acetate to a final concentration of 300 mM and then added a two-fold volume of ethanol, and stirred. Then, the mixture was kept still at −30° C. for 3 hr, and subjected to centrifugation at 10,000 rpm (9,000 g) for 10 min to obtain a DNA pellet. The thus obtained DNA pellet was dried in vacuo.

Step 2. Preparation of Plasmid pAG3 and Treatment thereof with Restriction Enzyme BamHI 20 units of restriction enzyme BamHI was added to 4 μg of the plasmid pAG3 DNA separated from *Corynebacterium melassecola* 22220 (deposited with the Fermentation Research Institute under the accession number FERM BP-559) and purified in substantially the same manner as in Example 1. The resulting mixture was reacted in 100 μl of buffer containing 10 mM Tris-HCl (pH 7.4), 10 mM MgSO$_4$, 50 mM NaCl and 1 mM dithiothreitol at a temperature of 37° C. for a period of 2 hr. Then, an equivolume of a 1:1 mixture of phenol and chloroform was added to the mixture and stirred, followed by recovery of an aqueous phase. To the aqueous phase was added an equivolume of chloroform and stirred, followed by recovery of an aqueous phase. To the aqueous phase was added sodium acetate to a final concentration of 300 mM and then added a two-fold volume of ethanol, and stirred. Then, the mixture was kept still at −30° C. for 3 hr, and subjected to centrifugation at 12,000 rpm (8,900 g) for 10 min to obtain a DNA pellet. The thus obtained DNA pellet was dried in vacuo.

Step 3. Isolation of plasmid pAG50

The whole amount of the DNAs obtained in Example 4 steps 1 and 2 was reacted with 3 units of T4 phage DNA ligase in 50 μl of buffer containing 50 mM Tris-HCl (pH 7.4), 10 mM MgCl$_2$, 10 mM dithiothreitol, 1 mM spermidine, 1 mM ATP and 0.1 mg/ml BSA at a temperature of 15° C. overnight. The temperature was elevated to 70° C., and the mixture was heated at 70° C. for 10 min to terminate the reaction.

Using 50 μl of the ligase reaction mixture, a tetracycline resistant transformant of *Corynebacterium melassecola* 801 (deposited with the Fermentation Research Institute under the accession number FERM BP-558) was obtained in accordance with the same transformation technique as employed in Example 2 step 2. The incubation in the regenerating medium was conducted for a period of 7 days. From the obtained tetracycline resistant transformant were separated plasmids in substantially the same manner as in Example 1, followed by analysis in substantially the same manner as in Example 2 step 2 except that EcoRI, HindIII, PstI, BamHI, SalI and XbaI were used as restriction enzymes. As a result, it was found that only one kind of plasmid was obtained.

The thus obtained plasmid was designated pAG50. The restriction enzyme SalI employed in this step is one purchased from Nippon Gene Co., Ltd., Japan. The restriction endonuclease cleavage map of this plasmid is illustrated in FIG. 7.

In substantially the same manner as mentioned above, the plasmid-cured strain of *Corynebacterium melassecola* 801 (deposited with the Fermentation Research Institute under the accession number FERM BP-558) was transformed using this plasmid to obtain a tetracycline resistant transformant. The restriction endonuclease cleavage map of the plasmid retained in the transformant was found to be the same as that of the plasmid incorporated in the above transformation.

EXAMPLE 5

Preparation of DNA fragments containing a gene for tetracycline resistance

Step 1. Preparation of a BamHI-EcoRI fragment having a molecular length of about 2.8 kb 20 μg of the plasmid pAG50 as prepared in Example 4 step 3 was digested with 100 units of BamHI and 100 units of EcoRI in 100 μl of a buffer containing 50 mM Tris-HCl (pH 7.4), 10 mM MgSO$_4$ and 100 mM NaCl at 37° C. for 2 hours to obtain digests. The digests were subjected to 1% (w/v) agarose gel electrophoresis in substantially the same manner as in Example 2 step 2 except that LMP agarose (manufactured and sold by Bethesda Research Laboratories, U.S.A.) was used and the electrophoresis was effected at 4° C. Then, the agarose gel was stained with ethidium bromide and subjected to ultraviolet radiation to visually detect the position of the digested DNA fragment. The DNA fragment was found at the position corresponding to the molecular length of about 2.8 kb. The agarose gel around the position of about 2.8 kb was cut off. To the thus obtained agarose gel was added to a 3-fold weight of a TE buffer and incubated at 65° C. for 10 minutes to completely dissolve the gel in the buffer. Then, to the thus obtained solution was added an equivolume of phenol. The mixture was stirred and an aqueous phase was recovered. To the aqueous phase was added an equi-volume of a phenol-chloroform (1:1) solution, followed by stirring. An aqueous phase was recovered, and to the aqueous phase was added an equivolume of chloroform, followed by stirring. An aqueous phase was recovered. To the aqueous phase was added sodium acetate so that the final concentration of sodium acetate became 300 mM, and then added a 2-fold volume of ethanol. The resulting mixture was allowed to stand at −30° C. for 3 hours. Then, the mixture was subjected to contrifugation at 10,000 rpm (9,000 g) for 10 minutes to obtain precipitates. The thus obtained precipitates were dried under reduced pressure to obtain about 3 μg of a DNA fragment. In substantially the same manner as in Referential Examples 1 and 2 mentioned above, it was confirmed that the DNA fragment thus obtained contained a gene for tetracycline resistance.

Step 2. Isolation of a BglII-SalI fragment having a molecular length of about 2.5 kb Substantially the same procedures as in Example 3 step 2 were repeated to obtain about 3 μg of a BamHI-BglII fragment having a molecular length of about 3.2 kb from the plasmid pAG14. The thus obtained DNA fragment was digested with 15 units of SalI in 30 μl of a buffer containing 50 mM Tris-HCl (pH 7.4), 10 mM MgSO₄ and 100 mM NaCl at 37° C. for 2 hours to obtain digests. The digests were subjected to 1% (w/v) agarose gel electrophoresis in substantially the same manner as in Example 2 step 2 except that LMP agarose (manufactured and sold by Bethesda Research Laboratories, U.S.A.) was used and the electrophoresis was effected at 4° C. Then, the agarose gel was stained with ethidium bromide and subjected to ultraviolet radiation to detect the position of the digested DNA fragment. The DNA was found at the position corresponding to the molecular length of about 2.5 kb. The agarose gel around the position of about 2.5 kb was cut off. To the thus obtained agarose gel was added to a 3-fold weight of a TE buffer and incubated at 65° C. for 10 minutes to completely dissolve the gel in the buffer. Then, to the thus obtained solution was added an equivolume of phenol. The mixture was stirred and an aqueous phase was recovered. To the aqueous phase was added an equi-volume of a phenol-chloroform (1:1) solution, followed by stirring. An aqueous phase was recovered, and to the aqueous phase was added an equivolume of chloroform, followed by stirring. An aqueous phase was recovered. To the aqueous phase was added sodium acetate so that the final concentration of sodium acetate became 300 mM, and then added a 2-fold volume of ethanol. The resulting mixture was allowed to stand at −30° C. for 3 hours. Then, the mixture was subjected to contrifugation at 10,000 rpm (9,000 g) for 10 minutes to obtain precipitates. The thus obtained precipitates were dried under reduced pressure to obtain about 1 μg of a DNA fragment. In substantially the same manner as in Referential Examples 1 and 2 mentioned above, it was confirmed that the DNA fragment thus obtained contained a gene for tetracycline resistance.

Step 3. Preparation of a EcoRI-SalI fragment having a molecular length of about 2.1 kb 20 μg of the plasmid pAG50 as prepared in Example 4 step 3 was digested with 100 units of EcoRI and 100 units of SalI in 100 μl of a buffer containing 50 mM Tris-HCl (pH 7.4), 10 mM MgSO₄ and 100 mM NaCl at 37° C. for 2 hours to obtain digests. The digests were subjected to 1% (w/v) agarose gel electrophoresis in substantially the same manner as in Example 2 step 2 except that LMP agarose (manufactured and sold by Bethesda Research Laboratories, U.S.A.) was used and the electrophoresis was effected at 4° C. Then, the agarose gel was stained with ethidium bromide and subjected to ultraviolet radiation to visually detect the position of the digested DNA fragment. The DNA fragment was found at the position corresponding to the molecular length of about 2.1 kb. The agarose gel around the position of about 2.1 kb was cut off. To the thus obtained agarose gel was added to a 3-fold weight of a TE buffer and incubated at 65° C. for 10 minutes to completely dissolve the gel in the buffer. Then, to the thus obtained solution was added an equivolume of phenol. The mixture was stirred and an aqueous phase was recovered. To the aqueous phase was added an equi-volume of a phenol-chloroform (1:1) solution, followed by stirring. An aqueous phase was recovered, and to the aqueous phase was added an equivolume of chloroform, followed by stirring. An aqueous phase was recovered. To the aqueous phase was added sodium acetate so that the final concentration of sodium acetate became 300 mM, and then added a 2-fold volume of ethanol. The resulting mixture was allowed to stand at −30° C. for 3 hours. Then, the mixture was subjected to contrifugation at 10,000 rpm (9,000 g) for 10 minutes to obtain precipitates. The thus obtained precipitates were dried under reduced pressure to obtain about 2 μg of a DNA fragment. In substantially the same manner as in Referential Examples 1 and 2 mentioned above, it was confirmed that the DNA fragment thus obtained contained a gene for tetracycline resistance.

What is claimed is:

1. An isolated plasmid, isolated from a glutamic acid-producing coryneform bacterium, *Corynebacterium melassecola* 22243 deposited with the Fermentation Research Institute, Japan under accession number FERM BP-560, which contains a gene for tetracycline resistance, said gene for tetracycline resistance being isolated from said glutamic acid-producing coryneform bacterium, and said gene having a property of imparting tetracycline resistance to a glutamic acid-producing coryneform bacterium and being capable of being used as a selective marker for a host-vector system using as a host a glutamic acid-producing coryneform bacterium.

2. The plasmid according to claim 1, which has a molecular length of about 20.4 kb and a restriction endonuclease cleavage map as shown in FIG. 1, and which is referred to as pAG1.

3. An isolated DNA fragment comprising a gene for tetracycline resistance which is isolated from a glutamic acid-producing coryneform bacterium, *Corynebacterium melassecola* 22243 deposited with the Fermentation Research Institute, Japan under accession number FERM BP-560.

4. A DNA fragment according to claim 3, which is a fragment derived from the plasmid pAG1 by fragmentation, said plasmid pAG1 having a molecular length of about 20.4 kb and a restriction endonuclease cleavage map as shown in FIG. 1.

5. A DNA fragment according to claim 4, which has a molecular length of about 2.1 kb and has one sticky end formed by EcoRI cleavage and the other sticky end formed by SalI endonuclease cleavage, and which has the following restriction sites:

a first PstI site and a second PstI site which are respectively located about 0.6 kb and about 1.5 kb from said sticky end formed by SalI cleavage.

* * * * *